(12) United States Patent
Itoi et al.

(10) Patent No.: US 8,247,639 B2
(45) Date of Patent: Aug. 21, 2012

(54) ABSORBENT ARTICLE

(75) Inventors: Namie Itoi, Tochigi (JP); Masahito Tanaka, Tochigi (JP); Shinsuke Nagahara, Tochigi (JP); Tetsuyuki Kigata, Tochigi (JP)

(73) Assignee: KAO Corporation, Tokyo (JP)

( * ) Notice: Subject to any disclaimer, the term of this patent is extended or adjusted under 35 U.S.C. 154(b) by 1119 days.

(21) Appl. No.: 10/586,314

(22) PCT Filed: Jan. 24, 2005

(86) PCT No.: PCT/JP2005/000834
§ 371 (c)(1),
(2), (4) Date: Aug. 8, 2008

(87) PCT Pub. No.: WO2005/070363
PCT Pub. Date: Aug. 4, 2005

(65) Prior Publication Data
US 2008/0287901 A1      Nov. 20, 2008

(30) Foreign Application Priority Data
Jan. 27, 2004   (JP) .................................. 2004-017924

(51) Int. Cl.
*A61F 13/15*        (2006.01)
(52) U.S. Cl. .......................... 604/372; 604/375; 604/368
(58) Field of Classification Search ................... 604/372, 604/375
See application file for complete search history.

(56) References Cited

U.S. PATENT DOCUMENTS

| | | | |
|---|---|---|---|
| 3,901,236 A | 8/1975 | Assarsson et al. | |
| 4,578,068 A | 3/1986 | Kramer et al. | |
| 4,822,453 A * | 4/1989 | Dean et al. ................. | 162/157.6 |
| 2003/0135177 A1 | 7/2003 | Baker | |

FOREIGN PATENT DOCUMENTS

| EP | 1088537 A2 | 4/2001 |
|---|---|---|
| EP | 1142696 A1 | 10/2001 |
| JP | 56-6098 Y2 | 2/1981 |
| JP | 56-65630 A | 6/1981 |
| JP | 61-62463 A | 3/1986 |
| JP | 63-73956 A | 4/1988 |

(Continued)

OTHER PUBLICATIONS

Notice of Rejection issued Apr. 21, 2009 in corresponding Japanese application No. 2005-014943.

*Primary Examiner* — Lynne Anderson
*Assistant Examiner* — Bradley Philips
(74) *Attorney, Agent, or Firm* — Birch, Stewart, Kolasch & Birch, LLP

(57) ABSTRACT

An absorbent article 1 has an extensible absorbent member 4 and is extensible as a whole. The absorbent member 4 has three-dimensionally dispersed therein a large number of small absorbent clusters 10a or 10b containing a superabsorbent polymer 11 and fibers 12, 13, 14. The small clusters 10a or 10b are dispersively arranged in a web containing crimped fibers. The small clusters include those composed of a superabsorbent polymer particle 11 and a large number of fibers 12 adhered to the particle 11 and those composed of a helically crimped fiber 13, a superabsorbent polymer particle 11, and fibers 14, the polymer particle 11 and the fibers 14 being taken into the helix of the crimped fiber 13.

8 Claims, 2 Drawing Sheets

FOREIGN PATENT DOCUMENTS

| | | |
|---|---|---|
| JP | 1-135350 A | 5/1989 |
| JP | 2-291858 A | 12/1990 |
| JP | 5-140848 A | 6/1993 |
| JP | 6-237956 A | 8/1994 |
| JP | 10-508225 A | 8/1998 |
| JP | 10-510447 A | 10/1998 |
| JP | 10-329252 A | 12/1998 |
| JP | 2001-340382 A | 12/2001 |
| WO | WO-91/09581 A1 | 7/1991 |
| WO | WO-96/109740 A1 | 4/1996 |
| WO | WO-97/01996 A1 | 1/1997 |
| WO | WO-01/74282 A1 | 10/2001 |

* cited by examiner

ABSORBENT ARTICLE

TECHNICAL FIELD

The present invention relates to absorbent articles such as sanitary napkins, panty liners, and incontinence pads.

BACKGROUND ART

Extensible absorbent articles such as sanitary napkins, panty liners, and incontinence pads are known (see, e.g., patent literature 1). The absorbent article according to patent literature 1 is characterized by having flexibility and capability of extending and contracting together with an undergarment.

Extensible absorbent members are also known (see, e.g., patent literature 2). The absorbent member of patent literature 2 has two extensible layers woven of elastic threads and a number of material bodies arranged in two dimensions between the layers, the material bodies being made of a superabsorbent material and fibrous fluff.
[Patent literature 1] WO96/10974
[Patent literature 2] WO91/09581

The absorbent article of patent literature 1 is designed to extend together with an undergarment to which it is attached but not be extended as much as a user wants when the user attaches it to the undergarment. In other words, the article is not designed to be used as extended to a size appropriate to the anatomy of an individual wearer's body. Nor it is given a device to prevent reduction of absorbency when it is extended.

The absorbent member of patent literature 2 generates gaps between the material bodies participating in absorption when it is extended. Therefore, the extended absorbent member will have lower absorbency than before being extended because liquid passes through the gaps.

DISCLOSURE OF THE INVENTION

The present invention provides an absorbent article including an extensible absorbent member and having extensibility as a whole. The absorbent member has a large number of small absorbent clusters containing a superabsorbent polymer and fibers dispersed therein in three dimensions.

The present invention also provides an extensible absorbent article that is designed not to be less absorbent when 150% extended in its longitudinal direction than before being extended.

The present invention also provides a stretchable absorbent member having a web containing crimped fibers. The web has a large number of small absorbent clusters containing a superabsorbent polymer particle and fibers. The small absorbent clusters are dispersed in the web in three dimensions.

DETAILED DESCRIPTION OF THE INVENTION

Figure 1:
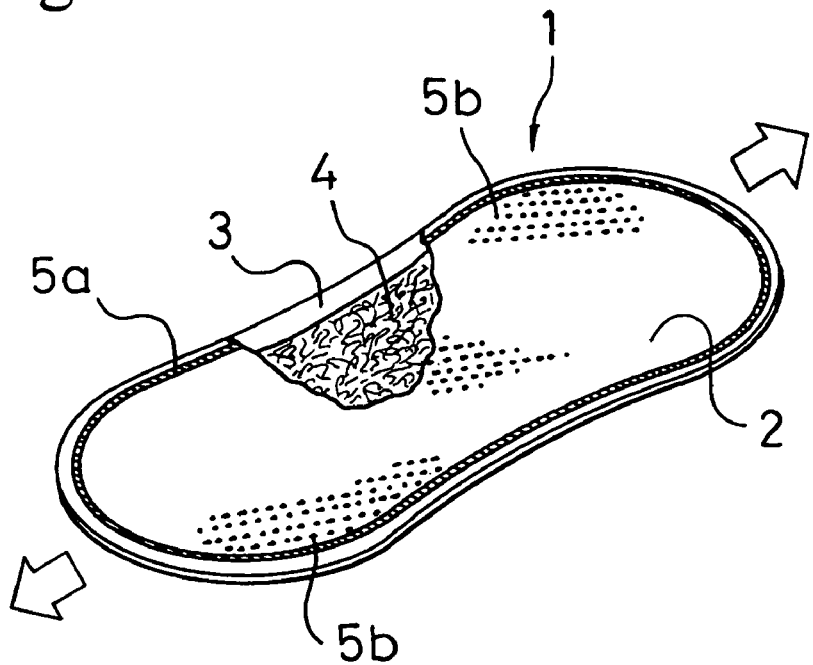
FIG. 1 is a perspective of a sanitary napkin as an embodiment of the absorbent article according to the present invention, with part cut away.

The present invention will be described with its preferred embodiment by way of the accompanying drawings. FIG. 1 represents a perspective of a sanitary napkin as an embodiment of the absorbent article of the invention, with part cut away. The sanitary napkin 1 according to the present embodiment is oblong and has a liquid permeable topsheet 2, a liquid impermeable backsheet 3, and a liquid retentive absorbent member 4 interposed between the sheets 2 and 3. The topsheet 2 and the backsheet 3 extent outward from both lateral sides and both longitudinal ends of the absorbent member 4 and are bonded to each other at the extensions with joining means such as heat sealing or a hot melt adhesive, whereby to form a circumferential seal 5a. The three members, i.e., the topsheet 2, backsheet 3, and absorbent member 4, are joined together by heat embossing in the area within the circumferential seal 5a to form a great number of dot joints 5b.

The napkin 1 is extensible in at least the longitudinal direction thereof, preferably in both the longitudinal and lateral directions thereof. When the napkin 1 is extensible about 120% in its longitudinal direction, the napkin 1 can be said to be extensible or to have extensibility. It is advantageous that the napkin 1 has contractibility as well as extensibility.

In order for the sanitary napkin 1 to have extensibility, it is necessary for every member constituting the napkin 1 to have extensibility. That is, all the topsheet 2, backsheet 3, and absorbent member 4 used in the present embodiment should be extensible.

The extensible topsheet 2 includes the nonwoven fabric described in commonly owned Japanese patent application JP-A-2002-187228. The nonwoven fabric has a two or more layered structure one layer of which contains self-crimping fibers having developed helical crimp. The nonwoven fabric has not only extensibility but contractibility owing to the presence of the fibers having developed helical crimp.

The extensible backsheet 3 includes a film capable of extending a few times the original size (but incapable of contracting) in both longitudinal and lateral directions, such as Nobix (trade name) manufactured by Iwaki Glass Co., Ltd. An extensible and contractible sheet, such as a urethane resin film having a weight of about 30 g/m$^2$, is also useful.

As stated in Background Art, an extensible absorbent member can be produced by various methods. However, a conventional extensible absorbent member reduces in thickness to have reduced absorbency when extended because an apparent reduction in thickness of the absorbent member leads directly to a reduction in absorption capacity of the absorbent member. Accordingly, in order for an absorbent member not to reduce in absorbency even when extended, a device is needed to prevent a reduction in thickness of an absorbent member from resulting in a reduction in absorption capacity. That is, an absorbent member should be designed (a) to be easily extensible without being accompanied by structural destruction and (b) to maintain its absorbency when extended. Hence, in the present invention, an extensible material is used as a constructional element (or a kind of a support) of an absorbent member, and a large amount of tiny absorbent elements with extremely high liquid absorbent and retentive properties are dispersed in the support in three dimensions.

The absorbent member 4 of the present embodiment contains a large number of small absorbent clusters (hereinafter referred to as small clusters or simply clusters) composed of a superabsorbent polymer particle and fibers. The small clusters are dispersively and uniformly disposed in three dimensions in the absorbent member 4. As an exemplary means for providing an absorbent member 4 with extensibility, the present embodiment adapts a configuration having a large number of small clusters dispersed in a web containing crimped fibers. In this case, the web containing crimped fibers corresponds to the above-mentioned "support". An absorbent member 4 having such a structure exhibits contractibility in addition to extensibility owing to the extensibility and contractibility of the crimped fibers. The weight ratio of the small clusters as absorbent elements to the crimped fibers as a support is preferably 20:80 to 60:40 in view of balance between absorbency and extensibility of the absorbent member 4.

When the absorbent member 4 of the present embodiment before being extended is seen from the topsheet side (the upper side), part of the absorbent elements are hidden under the absorbent elements existing above them. In absorbing a body fluid, it is the absorbent elements existing in the upper region that mostly bear the function of liquid absorption to prevent leakage. After the absorbent member is extended, on the other hand, the absorbent elements move in the horizontal direction with the horizontal extension of the support. It follows that the absorbent elements hidden below come to be seen from above and take participate in liquid absorption. In the way explained, the existence of a sufficient amount of absorbent elements in the absorbent member 4 makes it possible to secure absorption capacity based on a mechanism different from the apparent thickness (a simple capacity) of the absorbent member 4.

The small cluster as an absorbent element is made up of a superabsorbent polymer particle and a large number of fibers that are clustered to retain the shape as one tiny piece through mechanical entanglement or by the tackiness of the superabsorbent polymer developed on wetting.

As a result, the absorbent member 4, seen as a whole, has a dominantly high fiber density around a superabsorbent polymer particle and a relatively very low fiber density in the area of the support surrounding the clustered high-density fibers, thereby taking on a dual structure. Therefore, the structure of the absorbent member 4 of the present embodiment is such that capillarity increases toward the superabsorbent polymer particles and that the liquid received is swiftly absorbed and retained by the polymer. The structure is obviously different from a merely mixed state of superabsorbent polymer particles and fibers.

The capillarity of the small cluster does not change with the extension of the absorbent member 4 (or the support) because the small cluster itself neither extends nor contracts. In contrast, the absorbent member 4 (or the support) has its structure elongated when extended, and, as a result, has the fiber-to-fiber distance broadened, resulting in reduction of capillarity. In this situation, the small clusters, being in entanglement with the crimped fibers (i.e., the support), move with the extension of the absorbent member 4. Thus, as the absorbent member is extended, the difference in capillarity between the small clusters and the support becomes larger, which promotes migration of a body fluid to the polymer particles. As a result, the absorbent member tends to gain increased absorbency as a whole.

Figure 2A:
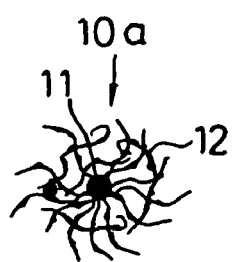
FIG. 2(a) schematically illustrates the structure of a small absorbent cluster.
Figure 2B:
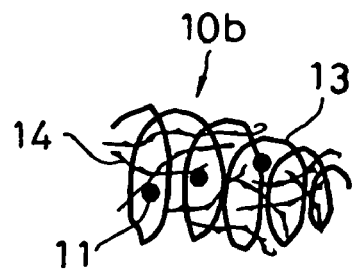
FIG. 2(b) schematically illustrates the structure of another type of a small absorbent cluster.

The small cluster that can be used in the present invention includes (a) a small cluster 10a shown in FIG. 2(a) that is composed of a superabsorbent polymer particle 11 and a large number of fibers 12 adhered to the particle 11 and (b) a small cluster 10b shown in FIG. 2(b) that is composed of a helically crimped fiber 13, a superabsorbent polymer particle 11, and fibers 14, the polymer particle 11 and the fibers 14 being taken into the helix of the crimped fiber 13. Both the small clusters of forms (a) and (b) described above are results of clustering of a superabsorbent polymer particle and fibers through mechanical entanglement and/or by the tackiness of the superabsorbent polymer developed on wetting.

The small cluster 10a (of form (a)) shown in FIG. 2(a) is obtained by, for example, mixing a particulate superabsorbent polymer 11 and fibers 12 with a relatively small amount of water, drying the mixture, and grinding the dried mixture to size. More specifically, an adequate amount of water is sprayed onto a stirred mixture of 100 parts by weight of a particulate superabsorbent polymer and 20 to 150 parts by weight of fibers. The particles of the superabsorbent polymer develop tackiness on contact with water, whereby the fibers stick to the superabsorbent polymer particles. Additionally, the superabsorbent polymer particles and the fibers are mechanically entangled with each other by the stirring. The mixture thus obtained is dried by drying means such as an electric dryer. The dried mixture is ground to size to obtain small clusters. The fibers are preferably hydrophilic ones. Pulp is particularly preferred. Hydrophobic fibers may be used in a small proportion in addition to the hydrophilic fibers.

The small cluster 10b shown in FIG. 2(b) has superabsorbent polymer particles 11 taken into the helical coil of a helically crimped fiber 13. According to necessity, the helically crimped fiber 13 preferably has other fibers 14, including hydrophilic fibers (e.g., pulp or cotton) and hydrophobic fibers, taken into its helix so that the small clusters may have a shorter fiber-to-fiber distance and a higher density. As a result, the small clusters will have increased capillarity and increased liquid drawing properties.

The small clusters 10b (of form (b)) shown in FIG. 2(b) are obtained by sprinkling superabsorbent polymer particles 11 on a web containing helically self-crimping fibers and other fibers 14 to prepare a composite (if desired, the composite is sprayed with water, followed by drying), cutting the composite into small pieces of a prescribed size, and applying heat to the pieces thereby crimping the self-crimping fibers to form helices and, at the same time, engulfing the particles 11 and the fibers 14 in the helices of the crimped fibers. Suitable examples of the helically self-crimping fibers include self-crimping conjugate fibers having an eccentric sheath/core configuration or a side-by-side configuration. Before being heated, the self-crimping fiber can be handled in the same manner as for ordinary fiber for nonwoven fabric and, upon being heated at a predetermined temperature, shrinks to develop a helical crimp. Specific examples of such self-crimping fiber are described in JP-A-9-296325 and Japanese Patent 2759331.

Preparation of the small clusters 10b (of form (b)) begins with making a web of helically self-crimping fibers and, if necessary, hydrophilic fibers such as pulp. A preferred weight ratio of the helically self-crimping fibers to the hydrophilic fibers is 10:0 to 4:6. Particles of a superabsorbent polymer are sprinkled on the web, and the web is broken into pieces, to which heat is applied. Heat application is carried out by drying in a dryer, blowing hot air or applying infrared rays. Heat application causes the self-crimping fibers in the small clusters to shrink to develop helical crimp. As described above, because each broken piece is a uniform mixture of the self-crimping fibers and the other fibers (e.g., pulp) with the superabsorbent polymer particles dispersed therein, the self-crimping fibers form a helix while taking the other fibers and the particles into the helix. There are thus obtained the small clusters of form (b). Before breaking the web into pieces, a small amount of water may be sprayed onto the web to stick the self-crimping fibers or hydrophilic fibers to the superabsorbent polymer particles, followed by drying to previously prepare a composite web.

In the preparation of the small clusters 10b (of form (b)), the amount of the superabsorbent polymer to be sprinkled preferably ranges from 10 to 50 parts by weight per 100 parts by weight of the web. The amount of water to be sprayed is preferably a few dozen parts by weight per 100 parts by weight of the particulate superabsorbent polymer. In either of the cluster forms (a) and (b), a fibrous superabsorbent polymer may be used in place of the particulate superabsorbent polymer. Using a fibrous superabsorbent polymer offers an advantage that entanglement with the hydrophilic fibers or the self-crimping fibers occurs more easily to provide small clusters that hardly ravel.

Whichever of forms (a) and (b) the small clusters may take, the size of the small clusters is, in average, preferably 5 mm or smaller, more preferably 2 mm or smaller, even more preferably 1.5 mm or smaller. Too large clusters can be difficult to three-dimensionally uniformly dispersed in the absorbent member 4. The lower limit of the size of the clusters is not particularly limited but is preferably 0.2 mm, more preferably 0.3 mm, even more preferably 0.5 mm. With this lower limit, neighboring small clusters will not be separated too far away from each other to retain the absorbency when the absorbent member is extended. Furthermore, reduction of capillarity of the support present among the small clusters, which is liable to occur when the absorbent member is extended excessively, is prevented. From these considerations, the size of the small clusters is preferably 0.2 to 5 mm, more preferably 0.3 to 2 mm, even more preferably 0.5 to 1.5 mm.

The absorbent member 4 which has a large number of the small clusters dispersively arranged in the web containing crimped fibers is preferably fabricated by methods (A) and (B) described below.

Method (A)

Small clusters and self-crimping fibers are air-laid at a predetermined mixing ratio to make a web. In view of the balance between absorbency and extensibility of the absorbent member 4, a preferred weight ratio of the small clusters to the self-crimping fibers is 20:80 to 60:40. As self-crimping fibers, the above-mentioned helically self-crimping fibers that are used to make the small clusters of form (b) are preferred. The resulting web is embossed all over with a pattern by ultrasonic embossing or heat embossing. A discrete embossing pattern, such as a dot pattern, is preferred. Heat is applied to the embossed web to cause the self-crimping fibers to self-crimp, which results in shrinkage of the web. To prevent excessive shrinkage of the web, it is preferred to fix the edges of the web by use of a pin tenter, etc. The absorbent member 4 thus obtained has the small clusters dispersed therein in three dimensions. The absorbent member exhibits not only extensibility but also contractibility.

Method (B)

A first web containing self-crimping fibers is fabricated. Small clusters are evenly sprinkled on the web. Another web containing self-crimping fibers is superposed on the clusters-sprinkled side of the first web. The operation of sprinkling small clusters followed by superposing a web is repeated once or more times to make a multilayer structure having a layer of the small clusters interposed between adjacent webs. The small clusters to self-crimping fibers ratio as used in method (A) applies to method (B). The same applies to the kind of the self-crimping fibers. The resulting multilayer structure (web) is embossed all over. Embossing can be performed in the same manner as in method (A). Thereafter, the same procedure as in method (A) is followed to obtain the absorbent member 4. The resulting absorbent member 4 has the small clusters dispersed therein in three dimensions similarly to that obtained by method (A). It has not only extensibility but contractibility.

Whichever of methods (A) and (B) may be adopted, the self-crimping fibers may be mixed up with up to about 20% by weight of hydrophilic fibers. The hydrophilic fibers as referred to herein include not only those made of hydrophilic materials, such as pulp and rayon, but also those made up of hydrophobic fibers of polyethylene terephthalate, polyethylene, polypropylene or a like resin material and having been treated with a hydrophilizing agent. Above all, rayon is suitable for ease of incorporating into the structure (ease of entangling) and improved absorbency.

The absorbent member 4 preferably has a weight of 150 to 800 g/m$^2$, more preferably 250 to 550 g/m$^2$, irrespective of the method of fabrication.

The absorbent member 4 has a large number of small clusters dispersed in a web containing crimped fibers. The web supporting the numerous small clusters preferably satisfies the following three conditions: (1) to have extensibility, (2) not to reduce in extensibility when wetted, and (3) to have low absorbing performance.

Reduction in extensibility described in (2) above is attributed to intermingling or bonding of fibers that might be caused by collapse or softening of fibers on wetting. The condition (3) is desired so that a significant reduction of absorbing performance may not occur when the absorbent member 4 is extended.

The conditions (1) to (3) are easily satisfied when the web is made up of synthetic fibers of various kinds (e.g., polyethylene terephthalate, polyethylene, polypropylene or a composite thereof) having been crimped three-dimensionally and thereby showing extensibility or crosslinked pulp. In order for the absorbent member 4 to have sufficient contractibility after being extended, in particular, it is more preferred that the web contain a large quantity of crimped fibers. Most desirably, the absorbent member 4 of the present embodiment has a web made solely of crimped fibers in which small clusters are dispersed. Nevertheless, the web may contain hydrophilic fibers in such a proportion as not to impair extensibility.

The crimped fiber-containing web having a large number of small clusters dispersed therein may be covered with an absorbent sheet to provide an absorbent member 4. To secure extensibility of the absorbent member 4, the absorbent sheet for covering is preferably formed of an extensible material. Useful extensible materials include a synthetic fiber web of polyethylene terephthalate, polyethylene, polypropylene or a composite thereof, nonwoven fabric prepared by heat embossing the synthetic fiber web with a discrete pattern such as a dot pattern, nonwoven fabric prepared by through-air thermal bonding the synthetic fiber web, and nonwoven fabric prepared by hydroentangling the synthetic fiber web. An elastic foamed material, such as polyurethane foam or polyethylene foam, having been hydrophilized is also useful.

Since the small clusters are dispersed in the absorbent member 4 in three dimensions, they certainly exist in every part of the absorbent member 4 when seen from above whether before or after extending. Therefore, unlike the absorbent member according to WO91/09581 described in Background Art, the absorbent member used in the present invention does not become less absorbent when extended than before being extended. On the contrary, the absorbent member can have increased absorbency by the extension because the distance between the small clusters increases with the extension to suppress gel blocking of the superabsorbent polymer. By the use of the absorbent member 4, the sanitary napkin according to the present embodiment is configured not to become less absorbent when 150% extended in its longitudinal direction than before being extended. The term "absorbency" as used herein means overall absorbing performance inclusive of various performance aspects required of an absorbent member such as liquid absorption capacity and absorption rate.

All the topsheet 2, backsheet 3, and absorbent member 4 having extensibility and contractibility, the sanitary napkin 1 of the present embodiment has extensibility and contractibility as a whole. The extensibility and contractibility of such an absorbent article (the napkin 1) are preferably such that, when the napkin 1 is 150% extended in its longitudinal direction, maintained in the extended state for 2 hours at 40° C. and 80% relative humidity, and released from the extended state, the length of the absorbent article measured after 20 seconds from the release is 130% to 150%, more preferably 130% to 140%, of the initial length and that the length of the absorbent article measured in the same manner as above but after 5 minutes from the release is 100% to 130%, more preferably 100% to 120%, of the initial length. In other words, it is preferred that the napkin 1 does not contract the moment it is detached from an undergarment but slowly contracts after the detachment. Thus, when the napkin 1 after use is removed from an undergarment for disposal, it slowly reduces in size. This is advantageous in that the absorbed liquid is prevented from being squeezed out immediately after the detachment and soiling the user's hand and that the napkin 1 can be disposed of in a compact form. The reason the napkin 1 slowly reduces in size is that body heat has been applied to the napkin 1 for a given period of time while worn whereby the fibers are heat set.

The sanitary napkin 1 of the present embodiment has a pressure-sensitive adhesive (not shown) applied to the surface of the backsheet 3 for attachment to an undergarment. The pressure-sensitive adhesive is preferably made of a material having rubbery elasticity, such as a styrene-butadiene-styrene (SBS) or styrene-ethylene-butadiene-styrene (SEBS) hot melt adhesive. To help extend and fix the extensible napkin 1 to an undergarment, the hot melt pressure sensitive adhesive is preferably applied in a discrete pattern, such as a pattern of circles, dots or polygons. Such a manner of adhesive application is also helpful for the napkin to extend and contract together with the undergarment such as panties to which it is fixed.

While the present invention has been described with reference to its preferred embodiment, it should be understood that the scope of the invention is not construed as being limited to the embodiment. Taking the form of the small clusters, for instance, while in the above embodiment the aforementioned cluster forms (a) and (b) are suitably used, other forms or structures may be used as long as a superabsorbent polymer and fibers are united into a body capable of retaining the form as a small cluster. For example, as long as the size falls within the above-recited proper range, any form in which a superabsorbent polymer and fibers are integrated into a unitary cluster can serve.

While in the above embodiment each of the topsheet 2, backsheet 3, and absorbent member 4 has both extensibility and contractibility, it is only necessary for these members to have at least extensibility. Where the sanitary napkin 1 has additional members other than these three members, such as a sublayer sheet intermediate between the topsheet 2 and the absorbent member 4, it is preferred for the sublayer sheet to have at least extensibility, too.

The absorbent article according to the present invention is not limited to sanitary napkins but includes panty liners, incontinence pads, and other like articles.

EXAMPLES

The present invention will now be illustrated in greater detail with reference to Examples, but it should be understood that the invention is not deemed to be limited thereto. Before entering into Examples, Preparation Examples for preparing small clusters are given.

Preparation Example 1

One gram of a superabsorbent polymer Aqualic CA (trade name) available from Nippon Shokubai Co., Ltd. was put into a 200 ml beaker. Water was sprayed on the polymer while stirring with a glass rod. To the polymer was added 2 g of pulp, and the stirring with the glass rod was continued while spraying additional water. The resulting mixture was taken out of the beaker and dried in an electric dryer at 110° C. for 2 hours. The dried mixture was ground to obtain small clusters shown in FIG. 2(a). The size of the small clusters was 1 mm in average and about 2 mm at the biggest.

Preparation Example 2

Two grams of helically self-crimping fibers CPP (trade name) from Daiwabo Co., Ltd. (fineness: 2.4 dtex; length: 51 mm) and 2 g of pulp were blended and opened on a card to obtain a web. One gram of a superabsorbent polymer Aqualic CA (trade name) from Nippon Shokubai Co., Ltd. was evenly sprinkled on the entire area of the web, and an appropriate amount of ion exchanged water was sprayed thereon, followed by drying spontaneously. The resulting composite was broken into about 100 pieces each weighing about 0.05 g. The pieces were heated in an electric dryer at 130° C. for 30 seconds, whereby the self-crimping fibers in the pieces shrank into helices while taking the pulp and the superabsorbent polymer particles into the helices. Small clusters illustrated in FIG. 2(b) were thus obtained. The small clusters measured 0.8 mm in average and about 2 mm at the biggest.

Preparation Example 3

Small clusters were obtained in the same manner as in Preparation Example 1, except that the degree of grinding was lowered so that the resulting small clusters measured 2 mm in size in average and about 5 mm at the biggest.

Preparation Example 4

Small clusters were obtained in the same manner as in Preparation Example 1, except that the degree of grinding was increased so that the resulting small clusters measured 0.6 mm in size in average and about 1.5 mm at the biggest.

Preparation Example 5

One gram of a superabsorbent polymer Aqualic CA (trade name) from Nippon Shokubai Co., Ltd. was put into a 200 ml beaker. Water was sprayed on the polymer while stirring with a glass rod. To the polymer was added 0.5 g of pulp, and the stirring with the glass rod was continued while spraying additional water. The resulting mixture was taken out of the beaker and dried in an electric dryer at 110° C. for 2 hours. The dried mixture was ground to obtain small clusters shown in FIG. 2(a). The size of the small clusters was 0.3 mm in average and about 0.5 mm at the biggest.

Reference Example 1

For Comparison

Aqualic CA (trade name), a superabsorbent polymer available from Nippon Shokubai Co., Ltd., was used as an absorbent element. The polymer had a particle size of 0.16 mm in average and 0.35 mm at the biggest.

Method of Measuring Size of Small Clusters:

Diameters of arbitrarily chosen 25 small clusters were measured with a microscope SZH-10 from Olympus Optical Co., Ltd. equipped with a CCD and connected to a CRT. The scale on the screen was decided beforehand using a stage micrometer (identification No. 422, 1 mm/100 div., from Erma Inc.). An average diameter and the maximum diameter of the 25 clusters chosen were obtained. Small clusters prepared by some methods, such as the method of Preparation Example 2, are irregular in shape, and some of small clusters may have fibrous matter sticking out. In such cases, the maximum length, inclusive of the fibrous matter, of the clusters is measured to obtain the maximum diameter of the biggest cluster and a number average diameter of the 25 clusters as representative sizes of the clusters.

Example 1

(1) Preparation of Absorbent Member

Figure 3:
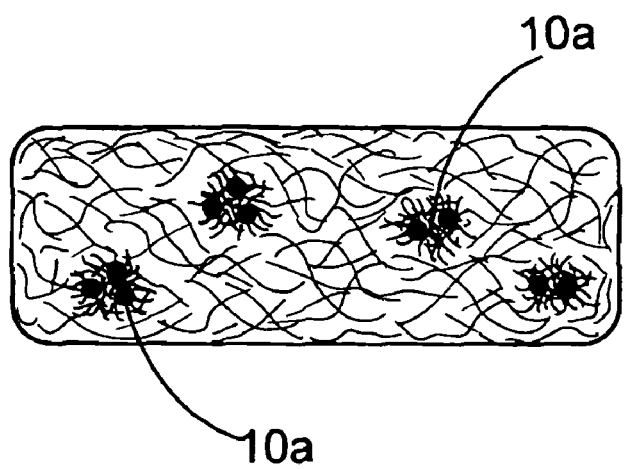
FIG. 3 schematically illustrates the structure of the absorbent member prepared in Example 1.

One point five grams of the small clusters obtained in Preparation Example 1 and 4 g of helically self-crimping fibers CCP (trade name, from Daiwabo) were simultaneously air laid to make a web measuring 15 cm by 30 cm and weighing 122 g/m². The web was subjected to ultrasonic embossing in a dot pattern. The embossed web was fixed on a pin tenter frame set at a width of 10 cm and a length of 20 cm and heated at 110° C. for 30 seconds, whereby the self-crimping fibers shrank to develop helical crimp. There was thus obtained an extensible and contractible absorbent member (FIG. 3) having a weight of 275 g/m².

(2) Preparation of Topsheet

Thermoplastic conjugate fibers SH (trade name) from Daiwabo were processed on a card to make a web weighing 12 g/m², which was used as an upper layer. The conjugate fibers SH were two-dimensionally crimped sheath/core conjugate fibers having polyethylene as a sheath and polyethylene terephthalate as a core.

Separately, helically self-crimping fibers CPP (trade name) from Daiwabo were processed on a card to make a web weighing 17 g/m², which was used as a lower layer.

The upper and lower layers were superposed on each other and joined in parts by ultrasonic embossing. The joints, each having a circular shape, were arranged in a rhombic lattice pattern. Hot air at 130° C.±10° C. was blown through the embossed web for 5 to 10 seconds, whereby the self-crimping fibers of the lower layer were helically crimped. As a result, the lower layer shrank, and the upper layer protruded between the joints, thereby to prepare nonwoven fabric having a large number of protrusions and weighing 58 g/m². The thus obtained extensible and contractible nonwoven fabric was used as a topsheet.

(3) Preparation of Backsheet

Flecmer (pellets available from The Nippon Synthetic Chemical Industry Co., Ltd.) was melt extruded to prepare a film weighing 20 g/m². The film was transparent, extensible and contractible and had a water vapor transmission rate of 2.0 g/(100 cm²·24 hr).

(4) Preparation of Sanitary Napkin

The backsheet, absorbent member, and topsheet were stacked in that order, heat sealed to form a circumferential seal 5a shown in FIG. 1, ultrasonically embossed to form a large number of dot joints 5b shown in FIG. 1, and trimmed along the circumferential seal 5a to obtain a sanitary napkin illustrated in FIG. 1. The absorbent member measured 5 cm in width and 12 cm in length. The napkin measured 6.5 cm in width and 14 cm in length. A hot melt pressure sensitive adhesive was applied to the surface of the backsheet in a pattern of 3 mm diameter circular dots.

Example 2

Figure 4:
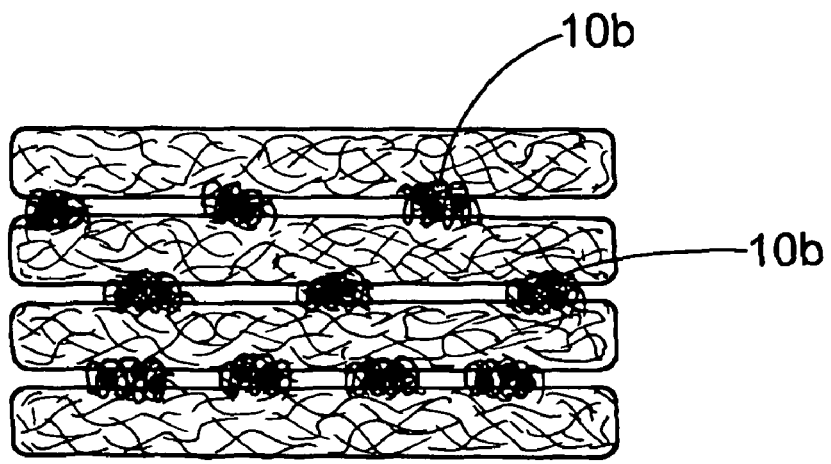
FIG. 4 schematically illustrates the structure of the absorbent member prepared in Example 2.

One gram of helically self-crimping fibers CPP (trade name) from Daiwabo were processed on a card to make a web measuring 30 cm by 45 cm and weighing 7.4 g/m². One gram of the small clusters obtained in Preparation Example 2 were evenly sprinkled on the web. The same web was superposed on the clusters-sprinkled side of the web. The operation of sprinkling small clusters followed by superposing a web was repeated twice more to make a multilayer structure composed of four webs and three layers of the small clusters each interposed between adjacent webs. The layered structure was joined by ultrasonic embossing in a dot pattern. The embossed structure was fixed on a pin tenter set at a width of 10 cm and a length of 20 cm and heated at 110° C. for 30 seconds, whereupon the self-crimping fibers in the webs were helically crimped to give an extensible and contractible absorbent member (FIG. 4) weighing about 350 g/m². A sanitary napkin illustrated in FIG. 1 was obtained in otherwise the same manner as in Example 1. The absorbent member measured 5 cm in width and 12 cm in length, and the napkin measured 6.5 cm in width and 14 cm in length.

Example 3

A sanitary napkin illustrated in FIG. 1 was obtained in the same manner as in Example 2, except for using the small clusters prepared in Preparation Example 3.

Example 4

A sanitary napkin illustrated in FIG. 1 was obtained in the same manner as in Example 2, except for using the small clusters prepared in Preparation Example 4.

Example 5

A sanitary napkin illustrated in FIG. 1 was obtained in the same manner as in Example 2, except for using the small clusters prepared in Preparation Example 5.

Comparative Example 1

Figure 5:
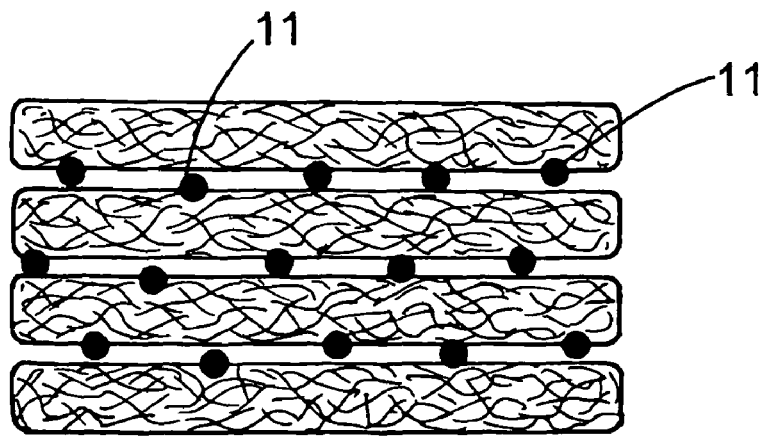
FIG. 5 schematically illustrates the structure of the absorbent member prepared in Comparative Example 1.

An absorbent member was prepared in the same manner as in Example 2, except for replacing the small clusters with the superabsorbent polymer of Reference Example 1 for comparison. The structure of the absorbent member is illustrated in FIG. 5. A sanitary napkin was produced in otherwise the same manner as in Example 1.

Comparative Example 2

One gram of pulp was air-laid to make a web measuring 30 cm by 45 cm and weighing 7.4 g/m². One gram of the small clusters obtained in Preparation Example 1 were evenly sprinkled on the web. The same pulp web was superposed on the clusters-sprinkled side of the web. The operation of sprinkling small clusters followed by superposing a web was repeated twice more to make a multilayer structure composed of four webs and three layers of the small clusters each interposed between adjacent webs. A sanitary napkin illustrated in FIG. 1 was produced using the resulting multilayered structure in the same manner as in Example 1.

Evaluation of Performance

The sanitary napkins obtained in Examples and Comparative Examples were evaluated by measuring (1) the amount of absorption in an initial state and in an extended state and (2) the length after 20 seconds and after 5 minutes from release from the extended state in accordance with the methods below.

(1) Amount of Absorption in Initial State and Extended State

Initial State:

The napkin was attached as such to a pair of panties, and the panties were put on a female mannequin. The mannequin was operated to take a walking movement at a speed of 100 steps/min, and 1 g of defibrinated horse blood was poured into the napkin for every one minute until it began to leak.

Extended State:

The napkin was tested in the same manner as described above, except it was attached to a pair of panties as 150% extended in its longitudinal direction.

The test was carried out in triplicate to obtain an average of the total amount of horse blood poured until leakage, which was taken as an absorption.

(2) Length after 20 Seconds and 5 Minutes

The napkin was 150% extended and fixed, as extended, to a 2 mm thick vinyl chloride plate at its both longitudinal ends with adhesive tape. The hot melt pressure sensitive adhesive layer on the surface of the backsheet was kept off the plate. The napkin was allowed to stand at 40° C. and 80% relative humidity for 2 hours and detached from the plate. The length of the napkin was measured 20 seconds and 5 minutes from the detachment. The test was carried out in triplicate to obtain an average length.

Commercially available ordinary sanitary napkins were inextensible.

As can be seen from the results of length measurement shown in Table 1, all the napkins of Examples slowly return to approximately their original length after they are held in an extended state in a worn condition thereof and released from the extended state.

INDUSTRIAL APPLICABILITY

Because of extensibility, the absorbent article of the invention can be extended in conformity to a wearer's body on use. While worn, therefore, it causes little discomfort to a wearer and snugly fits a wearer's body, hardly forming a gap with the body thereby to prevent leakage. Because the absorbent article is relatively small-sized before being extended, it is packaged into a compact size. The fact that one size fits wearers of various anatomies offers an advantage that the number of sizes available does not have to be overly increased. Where the absorbent article has contractibility as well as extensibility, it provides a further improved body fit and, after use, it shrinks for compact disposal.

The invention claimed is:

1. An absorbent article having extensibility as a whole and comprising an extensible absorbent member comprising a web having a number of small absorbent clusters dispersed therein in three dimensions, the small absorbent clusters containing a superabsorbent polymer and fibers; wherein the small clusters are each composed of a helically crimped fiber, a superabsorbent polymer particle, and other fiber, the polymer particle and the other fiber being taken into the helix of the helically crimped fiber;

wherein the other fiber comprises hydrophilic fiber;

wherein the small clusters have an average size of 0.2 to 5 mm; and wherein the extensible absorbent member has a fiber density around the small absorbent clusters that is higher than a fiber density around an area of support surrounding the small absorbent clusters.

2. The absorbent article according to claim 1, wherein the absorbent member is stretchable.

TABLE 1

|  |  | Example 1 | Example 2 | Example 3 | Example 4 | Example 5 | Comparative Example 1 | Comparative Example 1 |
|---|---|---|---|---|---|---|---|---|
| Absorption (g) | Initial | 7 | 7.7 | 7.1 | 7.7 | 7.1 | 5.5 | 7.2 |
|  | Extended | 8.3 | 10 | 7.1 | 8.3 | 5.1 | 2 | unmeasurable (inextensible absorbent member) |
| Length (mm) | Initial | 140 | 140 | 140 | 140 | 140 | 140 | 140 |
|  | 150% Extended | 210 | 210 | 210 | 210 | 210 | 210 | inextensible absorbent member |
|  | After 20 sec | 193 | 190 | 187 | 196 | 197 | 196 | inextensible absorbent member |
|  | After 5 mins | 166 | 153 | 150 | 168 | 168 | 166 | inextensible absorbent member |

As is apparent from the results of absorption shown in Table 1 above, the sanitary napkins of Examples are 150% extensible, and the absorbency of these napkins in the 150% extended state is as high as or higher than before the extension. It was revealed, in contrast, that the napkin of Comparative Example 1 of which the absorbent member does not have the small clusters reduces in absorbency when extended.

3. The absorbent article according to claim 1, wherein the absorbent member comprises a web containing crimped fibers, and the small absorbent clusters are dispersed in the web.

4. The absorbent article according to claim 1, wherein the small clusters are each composed of a superabsorbent polymer particle and a number of fibers adhered to the particle.

5. The absorbent article according to claim 4, wherein the small clusters are obtained by mixing particles of the superabsorbent polymer and the fibers with water, drying the mixture, and grinding the dried mixture to size.

6. The absorbent article according to claim 1, wherein the extensibility of the absorbent article is such that, when the absorbent article is 150% extended in its longitudinal direction, maintained in the extended state for 2 hours at 40° C. and 80% relative humidity, and released from the extended state, the lengths of the absorbent article measured after 20 seconds and after 5 minutes from the release are from 130% to 150% and from 100% to 130%, respectively, of the initial length.

7. The absorbent article according to claim 1, wherein the small absorbent clusters comprises hydrophilic fiber that is taken into a helical coil of a helically crimped fiber.

8. An absorbent article having extensibility as a whole and comprising a stretchable absorbent member comprising a web containing crimped fiber, the web having a number of small absorbent clusters dispersed in the web in three dimensions,
- wherein the small clusters are each composed of a helically crimped fiber, a superabsorbent polymer particle, and other fiber, the polymer particle and the other fiber being taken into the helix of the helically crimped fiber;
- wherein the other fiber comprises hydrophilic fiber;
- wherein the small clusters have an average size of 0.2 to 5 mm; and
- wherein the extensible absorbent member has a fiber density around the small absorbent clusters that is higher than a fiber density around an area of support surrounding the small absorbent clusters.

* * * * *